(12) United States Patent
Arp

(10) Patent No.: US 12,201,275 B2
(45) Date of Patent: Jan. 21, 2025

(54) ENDOSCOPY DEVICE HAVING A FLEXIBLE SHAFT

(71) Applicant: EvoEndo, Inc., Centennial, CO (US)

(72) Inventor: Scott R. Arp, Miami, FL (US)

(73) Assignee: EvoEndo, Inc., Centennial, CO (US)

( * ) Notice: Subject to any disclaimer, the term of this patent is extended or adjusted under 35 U.S.C. 154(b) by 22 days.

(21) Appl. No.: 18/108,562

(22) Filed: Feb. 10, 2023

(65) Prior Publication Data
US 2024/0268652 A1    Aug. 15, 2024

(51) Int. Cl.
| | |
|---|---|
| A61B 1/005 | (2006.01) |
| A61B 1/00 | (2006.01) |
| A61B 1/015 | (2006.01) |
| A61B 1/018 | (2006.01) |
| A61B 1/233 | (2006.01) |

(52) U.S. Cl.
CPC ............ *A61B 1/233* (2013.01); *A61B 1/0052* (2013.01); *A61B 1/0057* (2013.01); *A61B 1/015* (2013.01); *A61B 1/018* (2013.01)

(58) Field of Classification Search
CPC ..... A61B 1/233; A61B 1/0052; A61B 1/0057; A61B 1/015; A61B 1/018; A61B 1/055; A61B 1/2736; A61B 1/00011; A61B 1/00066
USPC ................................. 600/146, 149
See application file for complete search history.

(56) References Cited

U.S. PATENT DOCUMENTS

| | | | | |
|---|---|---|---|---|
| 4,996,974 A | * | 3/1991 | Ciarlei | A61B 1/0052 138/120 |
| 7,056,314 B1 | * | 6/2006 | Florio | A61M 25/0152 604/95.01 |
| 9,375,550 B2 | * | 6/2016 | Tegg | A61M 25/0136 |
| 2007/0156116 A1 | * | 7/2007 | Gonzalez | A61M 25/0136 604/528 |
| 2010/0168717 A1 | * | 7/2010 | Grasse | B29C 48/10 604/524 |
| 2010/0217257 A1 | * | 8/2010 | Howat | B32B 37/1284 606/41 |
| 2013/0038930 A1 | * | 2/2013 | Vent | G02B 23/2476 359/362 |
| 2013/0253268 A1 | * | 9/2013 | Okada | A61B 1/07 600/104 |
| 2014/0336572 A1 | * | 11/2014 | Heisel | A61M 25/0045 604/95.04 |
| 2015/0174363 A1 | * | 6/2015 | Sutermeister | A61M 25/005 604/95.04 |

(Continued)

*Primary Examiner* — Anh Tuan T Nguyen
*Assistant Examiner* — Rynae E Boler
(74) *Attorney, Agent, or Firm* — Farber LLC

(57) ABSTRACT

Systems and methods are disclosed for an endoscope for use in a surgical procedure, e.g., a pediatric trans-nasal endoscopy procedure. The endoscope may include a handle for gripping by a user, and a shaft extending from the handle. The shaft may have a working channel extending longitudinally therethrough and a distal region configured to be inserted into a patient. The exterior of the shaft may be protected by a laminate layer that is more flexible at the distal regions of the shaft than at more proximal regions, so as to improve steering. The shaft wall may be comprised of braided filaments so as to minimize the outer diameter of the shaft while maintaining a maximum working channel diameter. The handle may include symmetrical steering mechanisms to enable ambidextrous steering capabilities.

19 Claims, 9 Drawing Sheets

(56) References Cited

U.S. PATENT DOCUMENTS

| | | | |
|---|---|---|---|
| 2017/0224192 A1* | 8/2017 | Seto | A61B 1/00098 |
| 2018/0132703 A1* | 5/2018 | Reever | A61B 1/05 |
| 2020/0008687 A1* | 1/2020 | Friedlander | A61B 5/064 |
| 2022/0296077 A1* | 9/2022 | Mitsuhashi | A61B 1/0055 |

* cited by examiner

ENDOSCOPY DEVICE HAVING A FLEXIBLE SHAFT

BACKGROUND

Eosinophilic esophagitis (EoE) is an increasingly common chronic inflammatory disease that affects children and adults. Because of its potential to progress to esophageal stricture and the fact that symptoms do not always correlate with degree of eosinophilia, much attention has been paid to repeated assessment of the esophageal mucosa to ensure mucosal healing following treatment. In contrast, the risks, cost and time commitment associated with traditional sedated esophagogastroduodenoscopy (EGD) can be significant and have raised concerns for providers and patients alike. To address these questions, alternative methods are needed to measure esophageal inflammation. In addition to esophagoscopy with biopsies, other technologies such as the Cytosponge, esophageal string test and confocal tethered endomicroscopy have emerged as potential alternatives for assessing mucosal inflammation.

Recent work has led to the development of trans-nasal endoscopy/esophagoscopy (TNE) to assess the esophageal mucosa in adults. In contrast to traditional EGDs, TNE offers advantages, including that it can be performed in an outpatient clinic room, requires no anesthesia or sedation, uses an adult trans-nasal gastroscope that is tolerated by adults and procures samples adequate for assessment of Barrett's Esophagus. However, the endoscopes used in the adult procedures are not appropriate for use in pediatric setting and, in fact, may be too large for many adults.

During a trans-nasal endoscopic procedure, patients may experience physical discomfort due to the endoscope being inserted into the nose, through the sinus cavities and down into the esophagus. This physical discomfort, or even the fear of being uncomfortable, can make trans-nasal endoscopy procedures mentally and emotionally distressing for a patient, too. Because it is desirable to make the procedure mentally and physically easier on the patient, it would be advantageous to optimize the endoscope being used for the procedure.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The trans-nasal endoscope described hereinbelow, according to various embodiments, addresses various challenges. For example, the trans-nasal endoscope described hereinbelow, according to various embodiments, provides a device and associated methodology that can be used to adapt TNE to assess the esophageal mucosa, gastric, and duodenal, tracheal, and bronchial mucosa in children and small adults in both a sedated and unsedated manner with a full array of steering and visualization capabilities. The transnasal endoscope described hereinbelow, according to various embodiments, provides a scope that minimizes the outer diameter thereof, e.g., to reduce the discomfort to patients, while maximizing the diameter of the working channel, e.g., to provide the largest possible channel through which tools may be introduced, while simultaneously providing enhanced, e.g., four-way, steering capabilities as well as visualization functionality, as will be described more fully below. In various embodiments, the outer diameter of the endoscope shaft may be less than about 4.5 mm, and preferably is about 3.5 mm. In addition, in various embodiments, the diameter of the working channel may have a range of about 1.5 mm to 2.5 mm, and preferably is about 2.0 mm.

It is noted that, according to various embodiments, the endoscope described herein may be particularly well-suited for unsedated surgical procedures. Sedation is well-known, in certain circumstances, to present various risks to patients, but is often employed during surgical procedures to prevent a patient from experiencing discomfort or anxiety. By providing an endoscope having, e.g., a minimized outer diameter, a more flexible and more steerable distal regions (as will be explained in further detail below) among other advantages described below, patient discomfort and anxiety may be reduced, thereby enabling surgical procedures to be performed in an unsedated, and thus more safe, manner.

It should be recognized that, while the scope set forth herein is described hereinbelow for use in a trans-nasal endoscopy procedure, it may also be employed in a variety of other medical or surgical applications. For example, the scope set forth herein may be employed for use as a nasal endoscope, a trans-nasal esophagoscope, a trans-nasal gastroscope, a trans-nasal duodenoscope, a trans-nasal enteroscope, a triple endoscope, a bronchoscope, a laryngoscope, a trans-nasal gastroscope, an aerodigestive scope, and/or an endoscopic device used to visualize any body cavity into which it would fit, e.g., for examination of a stricture or the like. It should also be recognized that the endoscope described herein may be employed in fetal surgical procedures, and/or in surgical procedures that employ natural orifices, e.g., NOTES or natural orifice transluminal endoscopic procedures, such as trans-orally, trans-anally, trans-vaginally or any other natural orifice. The discussion herein of a pediatric trans-nasal endoscopy procedure is merely exemplary.

In accordance with various embodiments thereof, systems and methods are provided for use in a surgical procedure. In an embodiment, there is provided an endoscope for use in a surgical procedure, e.g., a pediatric trans-nasal endoscopy procedure, that includes a handle for gripping by a user, and a shaft extending from the handle. The shaft may have a working channel extending longitudinally therethrough. The shaft may also have a proximal region at or adjacent to the handle and a distal region configured to be inserted into a patient. In an embodiment, the exterior of the shaft may be protected by a laminate layer. The laminate layer of the proximal region of the shaft may have a first flexibility and the laminate layer of the distal region of the shaft may have a second flexibility that is more flexible than the first flexibility. In this way, the distal region of the shaft may be more flexible than the proximal region of the shaft for improved steering capabilities.

The shaft may have a shaft wall having an inner diameter defined by the working channel and an outer diameter that is adjacent to and enclosed by the laminate layer. The shaft wall may be comprised of braided filaments so as to minimize the outer diameter of the shaft wall while maximizing the diameter of the working channel, and thereby help enable the shaft to be configured for use in pediatric transnasal endoscopy procedures.

In further embodiments, the shaft may have a central region located longitudinally between the proximal region and the distal region. In this embodiment, the laminate layer of the central region may have a flexibility that may be more flexible than the first flexibility of the proximal region of the shaft, and that may be less flexible than the second flexibility of the distal region. In embodiments, the laminate layer of the distal region may be Pebax® 35D, the laminate layer of the central region may be Pebax® 55D, and the laminate layer of the proximal region may be Polyimide.

In further embodiments, the endoscope may also include at least one steering wire extending longitudinally within the shaft and parallel to the working channel. The steering wire may have a steering mechanism on the handle and may be actuatable by user to steer at least the distal region of the shaft. Still further, the endoscope may also include an illumination source and an imaging device, e.g., camera, located at the distal end of the shaft. The illumination source and the camera may be connected to and controlled by an electronic control module on the handle. An electrical cable may extend longitudinally within the shaft and parallel to the working channel. The endoscope may also include a control mechanism in the handle actuatable by a user to selectively control the flow of at least one of air, suction or water through the working channel. In embodiments, the working channel may include an instrument port through which a surgical instrument can be introduced into and through the working channel. In addition, the working channel may include a bifurcation region that splits the working channel into a first channel and a second channel. In this case, the first channel may have an instrument port through which a surgical instrument can be introduced into the working channel, and the second channel may be configured to convey at least one of air, suction or water into the working channel via a control mechanism in the handle actuatable by a user.

In still further embodiments, there is provided an endoscope for use in a surgical procedure, e.g., such as a pediatric trans-nasal endoscopy procedure, that includes a handle for gripping by a user and a shaft extending from the handle. The shaft may have a distal region configured to be inserted into a patient, and a shaft wall with an inner diameter and an outer diameter. The inner diameter may be defined by a working channel extending longitudinally through the shaft. The shaft may also include at least one wire extending longitudinally through the shaft wall between the inner diameter and the outer diameter. The shaft wall may be comprised of braided filaments that are woven over and under the at least one wire so as to maintain the at least one wire between the inner and outer diameters of the shaft wall.

In various embodiment, the at least one wire may be a steering wire actuatable by a user via a steering mechanism on the handle to steer at least the distal region of the shaft. Advantageously, the endoscope may have four steering wires, and the braided filaments of the shaft wall may be woven over and under the four steering wires so as to maintain the four steering wires between the inner and outer diameters of the shaft wall, while providing, e.g., four-way steering capabilities.

In various embodiments, the endoscope may also include an illumination source and an imaging device located at the distal end of the shaft. The illumination source and the imaging device may be connected to and controlled by an electronic control module on the handle. In this case, the at least one wire may be an electrical cable that connects the electronic control module to the illumination source and imaging device. In embodiments, the braided filaments of the shaft wall may be woven over and under the four steering wires and the electrical cable so as to maintain the four steering wires and the electrical cable between the inner and outer diameters of the shaft wall.

In some embodiments, the shaft may have a proximal region adjacent to the handle. The exterior of the shaft may be protected by a laminate layer. The laminate layer of the proximal region of the shaft may have a first flexibility and the laminate layer of the distal region of the shaft may have a second flexibility that is more flexible than the first flexibility. In this way, the distal region of the braided shaft may be more flexible than the proximal region of the shaft.

In various embodiments, the endoscope may also include a control mechanism in the handle. The control mechanism may be actuatable by a user to selectively control the flow of at least one of air, suction or water through the working channel. In addition, the working channel may include an instrument port through which a surgical instrument can be introduced into the working channel. Advantageously, the working channel may include a bifurcation region that splits the working channel into a first channel and a second channel. The first channel may have an instrument port through which a surgical instrument can be introduced into the working channel, and the second channel may be configured to convey at least one of air, suction or water into the working channel via a control mechanism in the handle that is actuatable by a user.

In still further embodiments, there is provided an endoscope for use in a surgical procedure, e.g., a pediatric trans-nasal endoscopy procedure. The endoscope may include a handle for gripping by a user, the handle having a steering control mechanism. The endoscope may also include a shaft extending from the handle. The shaft may have a working channel extending longitudinally therethrough. In addition, the shaft may have a distal region configured to be inserted into a patient. The endoscope may also include at least two steering wires extending longitudinally through the shaft and parallel to the working channel. The at least two steering wires may extend from the distal region of the shaft to the steering control mechanism of the handle. Still further, the steering control mechanism may include first and second actuators located on opposite sides of the handle. The first and second actuators may be actuatable by a user to allow ambidextrous steering of at least the distal region of the shaft.

In embodiments, the first and second actuators may control steering of the distal region of the shaft in the left and right directions. The first and second actuators may include first and second rollers, the first and second rollers each having one of the at least two steering wires attached thereto. The steering mechanism may also include a third actuator configured to control steering of the distal region of the shaft in the up and down directions. In this case, the endoscope may include a third steering wire to which the third actuator may be attached. The third actuator may include a thumb knob extending from the proximal end of the handle. The endoscope may also include a steering collar located at the distal region of the shaft. The steering wires may be connected to the steering collar at circumferentially spaced apart locations. The steering wires may be pulled by the actuators so as to selectively move such locations of the steering collar to steer the distal region of the shaft.

In various embodiments, the endoscope also includes a control mechanism in the handle actuatable by a user to selectively control the flow of at least one of air, suction or water through the working channel. Furthermore, the endoscope may also include an illumination source and an imaging device located at a distal end of the shaft. The illumination source and the imaging device may be connected to and controlled by an electronic control module on the handle via an electrical cable. The electrical cable may extend longitudinally within the shaft and parallel to the working channel. In addition, the working channel may include an instrument port through which a surgical instrument can be introduced into the working channel.

It should be noted, of course, that to the extent that images, e.g., image signals, image data, etc., are described herein, it will be understood that such also refers to video, e.g., video signals, video data, etc., and that the description of the image signals is intended to include single images, still images, video images, etc. without limitation.

DRAWINGS

DETAILED DESCRIPTION

Reference will now be made in detail to specific embodiments illustrated in the accompanying drawings. In the following detailed description, numerous specific details are set forth to provide a thorough understanding. However, it will be apparent to one of ordinary skill in the art that embodiments may be practiced without these specific details. In other instances, known methods, procedures, components, circuits, and networks have not been described in detail so as not to unnecessarily obscure aspects of the embodiments.

Figure 1:
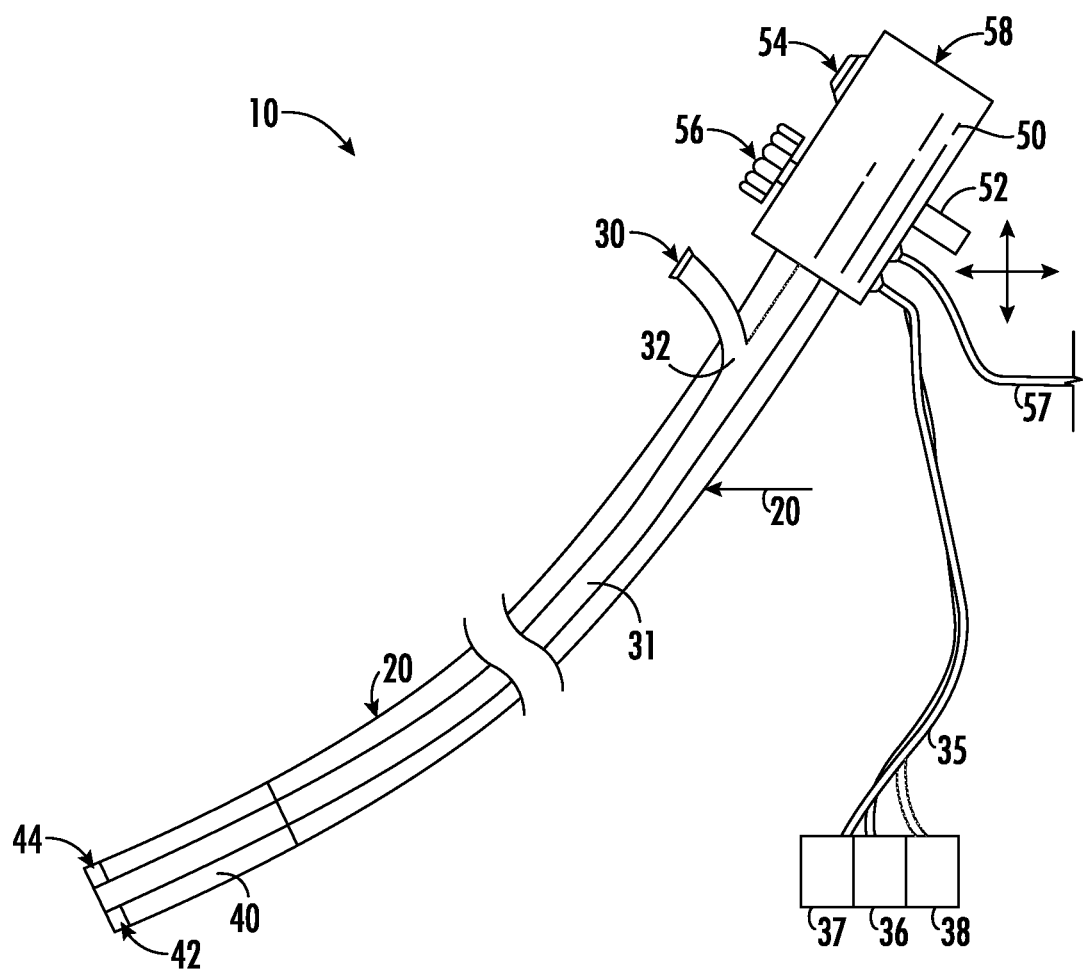
FIG. 1 shows a schematic representation of a trans-nasal endoscope that includes a flexible endoscope shaft, in accordance with various embodiments.

FIG. 1 is a schematic diagram of a trans-nasal endoscope 10, according to one example embodiment, illustrating some of the various features thereof. As mentioned previously, while the example embodiments set forth hereinbelow are described as an endoscope that is suitable for trans-nasal insertion into a patient, and is particularly well-suited for trans-nasal insertion into a child or small adult, it is understood that this is merely one example embodiment, and that the description hereinbelow of a trans-nasal endoscope does not preclude the use of the device in other types of procedures and for other types of patients. It should be noted that FIG. 1 is merely schematic, and thus the shape and position of the various features illustrated therein are merely exemplary. Additional figures, illustrating specific embodiments of the various features and functionality, will be provided in further detail below.

In the embodiment shown schematically in FIG. 1, the trans-nasal endoscope 10 includes a flexible endoscope shaft 20. The flexible endoscope shaft 20 has a working channel 31. The working channel 31 extends longitudinally from a distal end 40 of the endoscope shaft 20 proximally towards a handle 50 located at or near the proximal end of the trans-nasal endoscope 10. At, within or near the handle 50, the working channel 31 has a bifurcation region 32. Proximal to the bifurcation region 32, the working channel 31 splits into two channels. A first portion of the working channel 31 proximal to the bifurcation regions 32 extends towards an instrument insertion port 30 suitable for, e.g., conducting a biopsy therethrough. The instrument insertion port 30 allows an instrument, e.g., a pediatric nasal endoscope biopsy forceps or other medical device, to be inserted through the bifurcation region 32 and to, and past, the distal end 40 of the endoscope shaft 20 so as to perform a procedure, e.g., a biopsy procedure, on tissue located at or near to the distal end 40 of the endoscope shaft 20.

A second portion of the working channel 31 proximal to the bifurcation regions 32 extends towards an air, water and suction (AWS) control mechanism 52. The AWS control mechanism 52 includes various valves (not shown in this view, but shown and described more fully in Applicant's co-pending patent application having client matter number EVO 1007-US, the disclosure of which is incorporated by reference herein in its entirety, and being filed concurrently with the present application) that allow selective connection of the working channel 31 to the AWS tubing set 35. The AWS tubing set 35 may include one or more flexible tubes (shown and described in greater detail in Applicant's co-pending patent application having client matter number EVO 1007-US). The AWS tubing set 35 may be connected to a water source 37 for supplying water through the working channel 31, to a suction source 36 for supplying suction through the working channel 31, and/or to an air source 38 for supplying air through the working channel 31, depending upon a user's selection via the AWS control mechanism 52. More specifically, the AWS control mechanism allows a user to direct one or more of air, suction or water through, e.g., the bifurcation region 32 and to, and past, the distal end 40 of the endoscope shaft 20 so as to enable their use during the performance of a procedure on tissue located at or near to the distal end 40 of the endoscope shaft 20.

The distal end 40 of the endoscope shaft 20 also includes an illumination source 42 to provide light at the distal tip 40. In embodiments, the illumination source 42 may be connected to and at least partially controllable by an electronics control module 54 located in the handle 50. The distal end 40 of the endoscope shaft 20 also includes an image capture device 44 to convey image or video signals related to the region of the distal end 40 of the endoscope shaft 20. In embodiments, the image capture device 44 may also be connected to and at least partially controllable by the electronics control module 54 located in the handle 50. The handle 50 may also include a shaft steering mechanism 56 to control or steer the lateral displacement at the distal end 40 of the endoscope shaft 20. In addition, the handle 50 may include a video display output cable 57, which may be connected to and output image data to a separate image or video display or control unit (not shown in this view).

Figure 2:
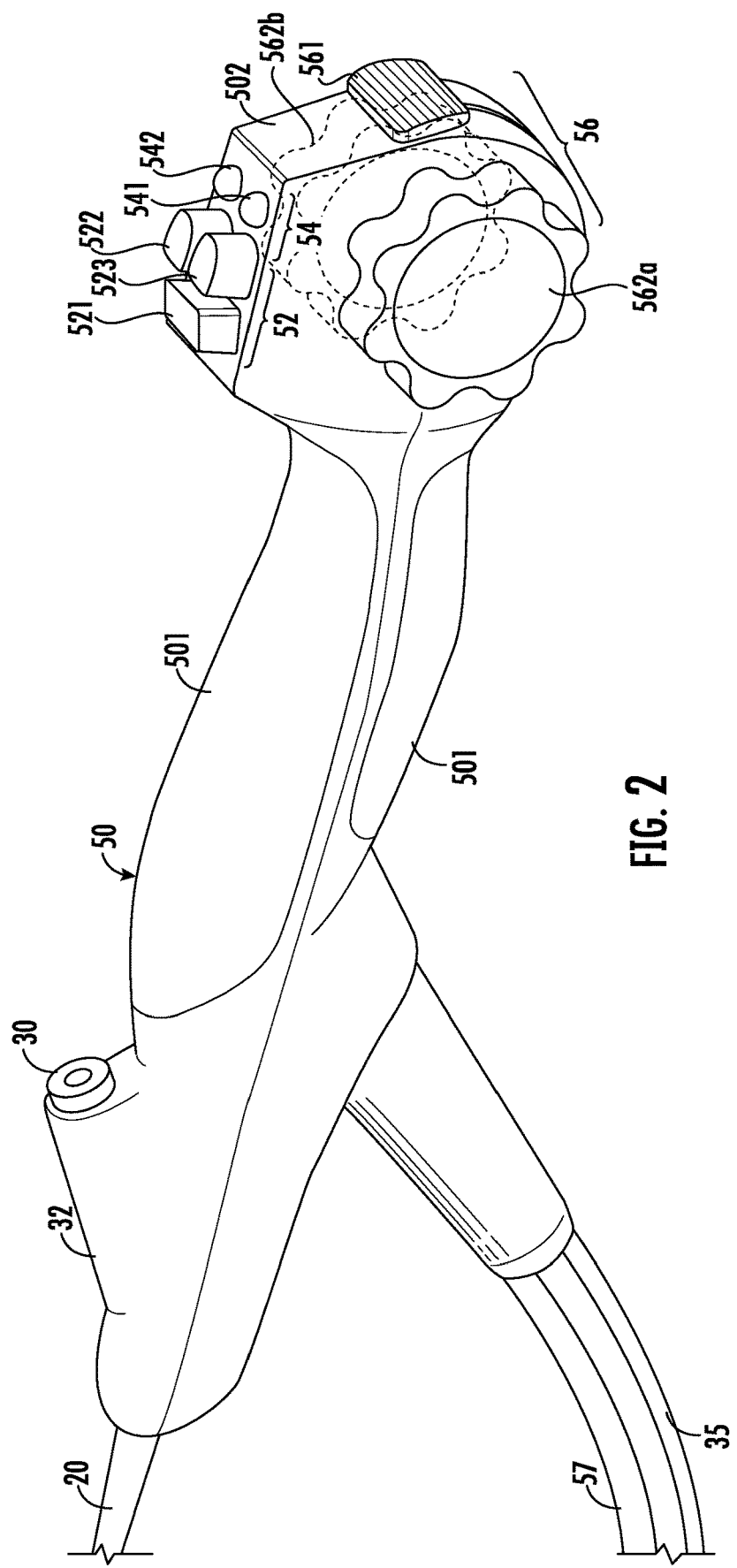
FIG. 2 is a perspective view of the handle of the trans-nasal endoscope, in accordance with various embodiments.

FIG. 2 is a perspective view of an example embodiment of the handle 50 of the trans-nasal endoscope 10. In this embodiment, the features and functionality that were shown schematically in FIG. 1 are provided in more detail, showing additional advantages thereof. For example, in this embodiment, the handle 50 of the trans-nasal endoscope 10 includes a gripping region 501 sized and contoured to fit comfortably in a user's hand. Located distally relative to the gripping region 501 is the bifurcation region 32. From the distalmost end of the bifurcation region 32 extends the flexible endoscope shaft 20, having a portion of the working channel 31 extending therethrough. The working channel 31 extends from the distal end 40 of the endoscope shaft 20, and splits into two channels in the bifurcation region 32. A first portion of the working channel 31 extends towards the instrument insertion port 30, which is suitable for receiving an instrument, e.g., a pediatric nasal endoscope biopsy forceps or other medical device, therethrough. The second portion of the working channel 31 proximal to the bifurcation region 32 extends proximally through the interior of the gripping region 501.

Proximal to the gripping region 501 is a control region 502 sized and shaped to extend beyond the heel of the user's hand when the palm of the user's hand is gripping the gripping region 501, enabling the control features positioned on the control region 502 to be engaged by the user's second hand when the user's first hand is gripping the gripping region 501.

In the embodiment shown in FIG. 2, the control region 502 has various control features positioned thereon. For example, the control region 502 has the AWS control mechanism 52. As set forth above, the AWS control mechanism 52 includes various features, e.g., buttons, valves, etc., that allow selective connection of the air, water and suction supply sources 36, 37, 38 to the working channel 31 via respective flexible tubes of the AWS tubing set 35. In the embodiment shown in FIG. 2, the AWS control mechanism 52 includes an air supply control button 521. The air supply control button 521 functions to selectively connect the air source 38 to the working channel 31, as is described in greater detail in Applicant's co-pending patent application having client matter number EVO 1007-US.

In the embodiment shown in FIG. 2, the AWS control mechanism 52 also includes a water supply control button 522. The water supply control button 522 functions to selectively connect the water source 37 to the working channel 31, as is described in greater detail in Applicant's co-pending patent application having client matter number EVO 1007-US.

Still further, in the embodiment shown in FIG. 2, the AWS control mechanism 52 includes a suction supply control button 523. The suction supply control button 523 functions to selectively connect the suction source 36 to the working channel 31, as is described in greater detail in Applicant's co-pending patent application having client matter number EVO 1007-US.

In the embodiment shown in FIG. 2, the control region 502 also has the electronics control mechanism 54. As set forth above, the electronics control mechanism 54 includes various features, e.g., buttons, electrical connections, etc., that allow selective operation of, e.g, the image capture device 44 and/or the illumination device 44 located at the distal end 40 of the endoscope shaft 20. In the embodiment shown in FIG. 2, the electronics control mechanism 54 includes a first, e.g., a white balance control, button 541. In this embodiment, the white balance control button 541 functions to selectively control a white balancing operation by sending a corresponding signal to an image or video control unit (not shown), as is described in greater detail in Applicant's co-pending patent application having client matter number EVO 1009-US, the disclosure of which is incorporated by reference herein in its entirety, and being filed concurrently with the present application.

In the embodiment shown in FIG. 2, the electronics control mechanism 54 also includes a second, e.g., an image capture control, button 542. In this embodiment, the image capture control button 542 functions to selectively control the capture of image or video signals sent by the image capture device 44, e.g., such as by providing a signal to an image or video display or control unit (not shown), as is described in greater detail in Applicant's co-pending patent application having client matter number EVO 1009-US.

In the embodiment shown in FIG. 2, the control region 502 also has the shaft steering mechanism 56. As set forth above, the shaft steering mechanism 56 includes various features, e.g., knobs, rollers, etc., that allow a user to control or steer the lateral displacement at the distal end 40 of the endoscope shaft 20. In the embodiment shown in FIG. 2, the shaft steering mechanism 56 includes a first knob 561 for controlling a first movement of the distal end 40 of the endoscope shaft 20, as will be described in greater detail below in connection with FIG. 8. FIG. 2 also illustrates the shaft steering mechanism 56 including opposing roller knobs 562a, 562b (knob 562b being hidden from view in FIG. 2, but being located on the opposite side of the handle 50) for controlling additional movements of the distal end 40 of the endoscope shaft 20, as will be described in greater detail below in connection with FIGS. 7a and 7b.

In addition, in the embodiment shown in FIG. 2, the handle 50 of the trans-nasal endoscope 10 includes a connection to the AWS tubing set 35. As set forth above, the AWS tubing set includes various flexible tubes that connect to the suction source 36, the water source 37 and the air source 38, as is described in greater detail in Applicant's co-pending patent application having client matter number EVO 1007-US. Still further, the handle 50 includes a connection to a video display output 57, e.g., for connecting to and outputting image data to a separate video display or control unit (not shown in FIG. 2). In the embodiment shown in FIG. 2, the video display output 57 is bundled together with the AWS tubing set 35, as is described in greater detail in Applicant's co-pending patent application having client matter number EVO 1009-US.

Figure 3:
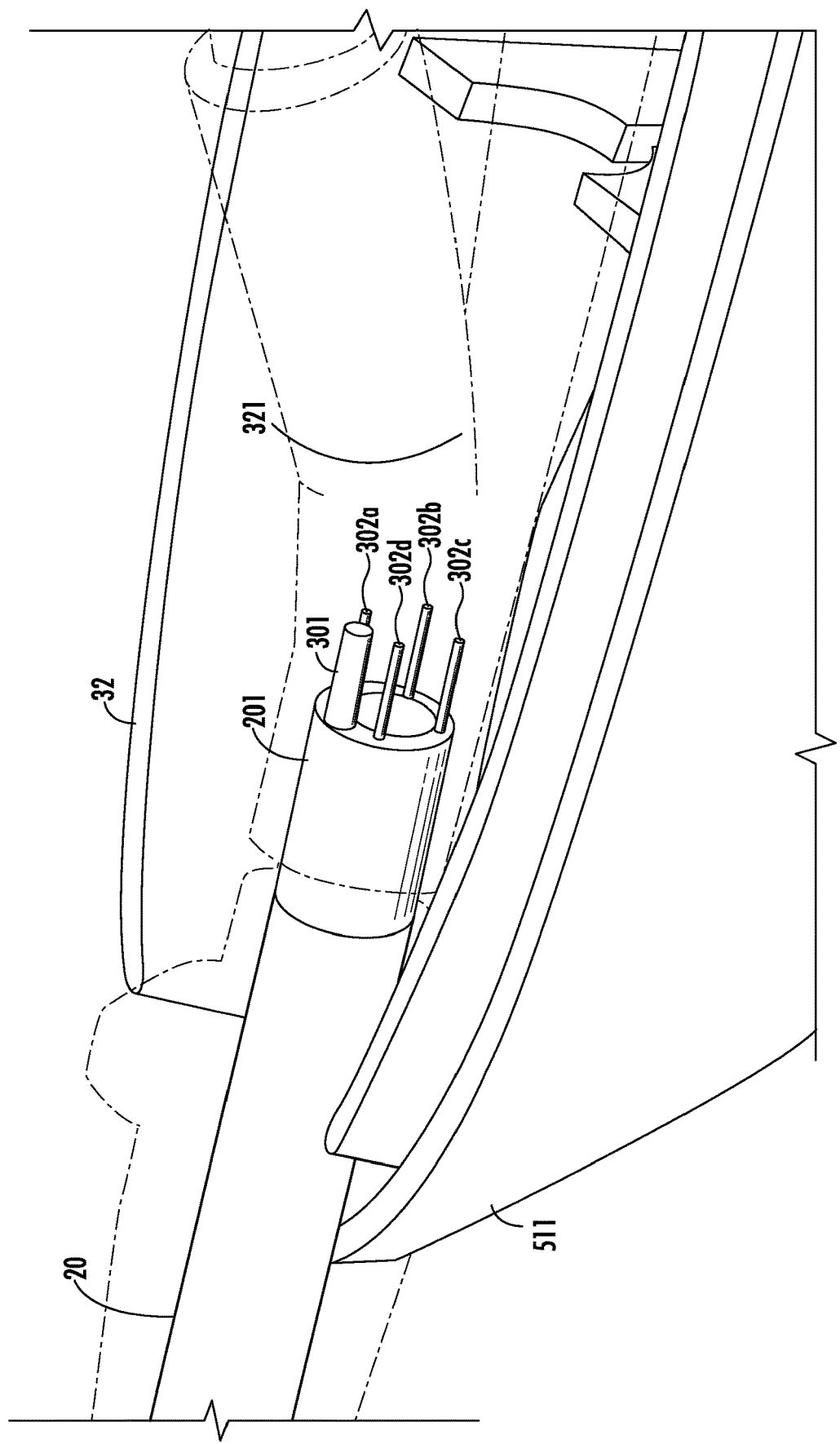
FIG. 3 is a perspective, cut-away view of a handle in the vicinity of a bifurcation region, in accordance with various embodiments.

FIG. 3 is a perspective, cut-away view of the handle 50 in the vicinity of the bifurcation region 32. In the embodiment shown in FIG. 3, the endoscope shaft 20 terminates at a location 201 that is slightly proximal relative to the distalmost end 511 of the handle 50, but also slightly distal relative to the location 321 at which the working channel 30 splits into two channels. In this embodiment, while the endoscope shaft 20 terminates at this location, it can be seen in FIG. 3 that several components that are incorporated into the endoscope shaft 20 continue to extend proximally beyond this location. Specifically, it can be seen in FIG. 3 that a camera electrical cable 301, that is embedded in, or otherwise disposed within, the wall of the endoscope shaft 20 extends proximally beyond this location towards the electronic control device 54 that is located at a more proximal location within the handle 50 (it should be noted that only a partial view of the camera electrical cable 301 is shown in FIG. 3). The camera electrical cable 301 extends longitudinally along the length of the endoscope shaft 20 so as to be parallel to the working channel 30 that is also running longitudinally through the endoscope shaft 20.

Several other components that are incorporated into the endoscope shaft 20 also continue to extend proximally beyond the location 201 and the location 321 at which the working channel 30 splits into two channels. Specifically, it can be seen in FIG. 3 that, in this embodiment, four steering wires 302a, 302b, 302c, 302d, that are embedded in, or otherwise disposed within, the wall of the endoscope shaft 20 extend proximally beyond this location towards the shaft steering mechanism 56 that is located at a more proximal location within the handle 50 (it should be noted that only a partial view of the four steering wires 302a, 302b, 302c, 302d are shown in FIG. 3). The four steering wires 302a, 302b, 302c, 302d extend longitudinally along the length of the endoscope shaft 20 so as to be parallel to the working channel 30 that is also running longitudinally through the endoscope shaft 20.

Figure 4:
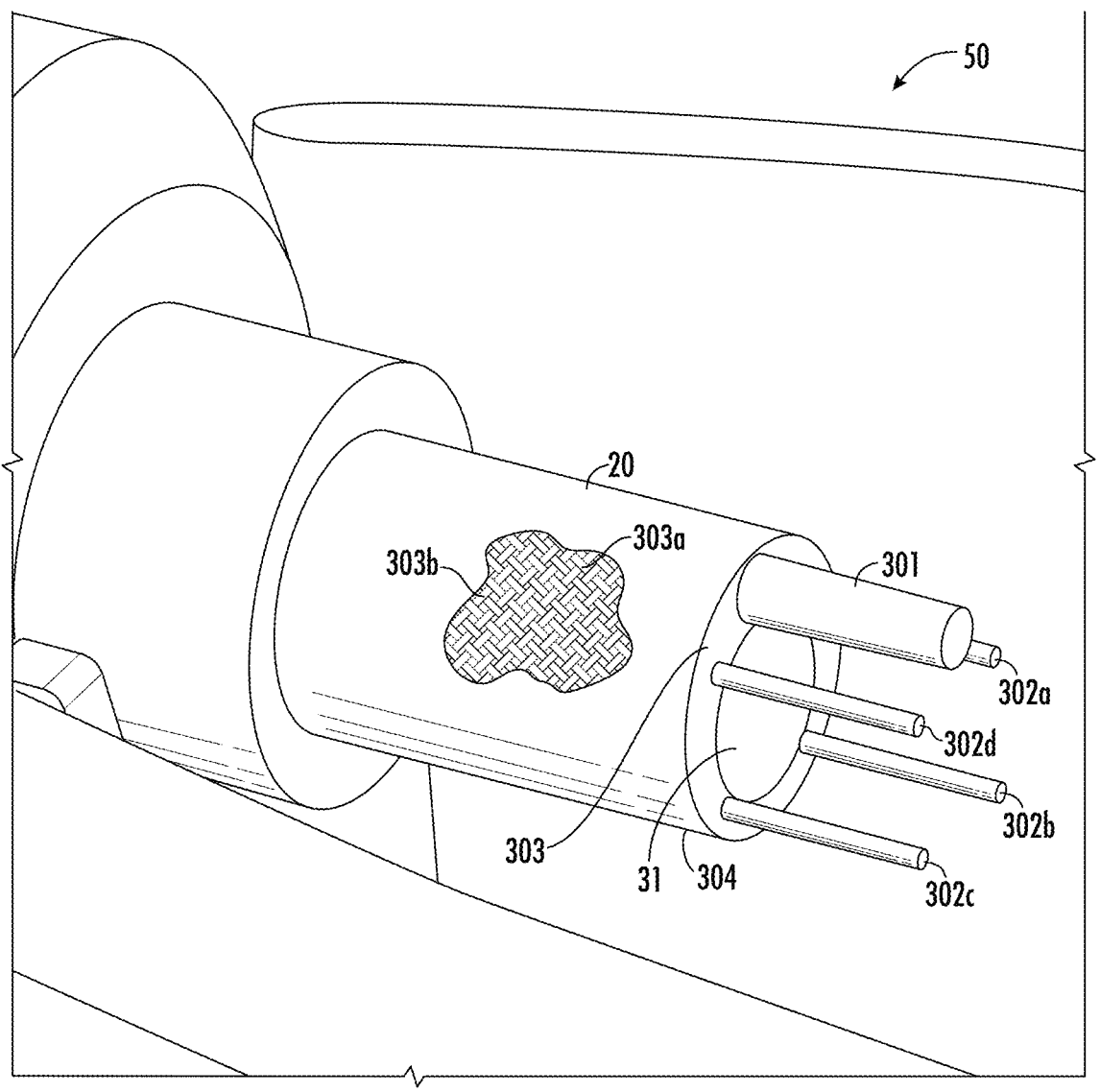
FIG. 4 is perspective, cut-away view of the handle in the vicinity of the bifurcation region, enlarged to show additional details of various components of the endoscope shaft, in accordance with various embodiments.

FIG. 4 is another perspective, cut-away view of the handle 50 in the vicinity of the bifurcation region 32, but enlarged in comparison to FIG. 3 so as to show additional details of the various components of the endoscope shaft 20. Specifically, it can be seen in FIG. 4 that the camera electrical cable 301, as well as the four steering wires 302a, 302b, 302c, 302d, are disposed within the wall of the endoscope shaft 20 so as to each be located laterally adjacent to the working channel 30. In the embodiment shown, the camera electrical cable 301 is, in the view shown, positioned at the top-most circumferential position of the endoscope shaft 20, so as to be at, e.g., a 12 o'clock or 0 degree position along the outer circumference of the working channel 30. In this embodiment, the camera electrical cable 301 maintains this same top-most circumferential position relative to the working channel 30 along the full length of the endoscope shaft 20 so as to also be in the top-most circumferential position relative to the working channel 30 at the distal end 40 of the endoscope shaft 20, where it connects to the illumination source 42 and the image capture device 44 (as is described in greater detail in Applicant's co-pending patent application having client matter number EVO 1009-US).

Likewise, as can be seen in FIG. 4, the four steering wires 302a, 302b, 302c, 302d are also disposed within the wall of the endoscope shaft 20 so as to each be located laterally adjacent to the working channel 30. In the embodiment shown, the four steering wires 302a, 302b, 302c, 302d are, in the view shown, positioned 90 degrees apart relative to each other, with the steering wires 302a and 302d each being spaced 45 degrees apart from the camera electrical cable 301 that is located at the top-most circumferential position of the endoscope shaft 20. For example, in this embodiment, the first steering wire 302a is located at, e.g., a 45 degree clockwise position relative to the top-most position along the outer circumference of the working channel 30. The second steering wire 302b is located at, e.g., a 135 degree clockwise position relative to the top-most position along the outer circumference of the working channel 30. The third steering wire 302c is located at, e.g., a 225 degree clockwise position relative to the top-most position along the outer circumference of the working channel 30, and the fourth steering wire 302d is located at, e.g., a 315 degree clockwise position relative to the top-most position along the outer circumference of the working channel 30. In this embodiment, the four steering wires 302a, 302b, 302c, 302d maintain their respective circumferential positions relative to the working channel 30 along the full length of the endoscope shaft 20 so as to also be in the 45, 135, 225 and 315 degree positions, respectively, relative to the working channel 30 at the distal end 40 of the endoscope shaft 20, where they connect to a steering collar (as will be shown and described in connection with FIG. 6).

Of course, it should be recognized that the endoscope shaft 20 may, in alternative embodiments, have more than one electrical cable extending longitudinally therethrough, depending on the arrangement and functionality of the illumination source and the camera componentry located at the distal end thereof. Likewise, it should be recognized that, in the embodiment shown having four steering wires extending longitudinally therethrough, these four steering wires may be circumferentially arranged within the shaft 20, and/or may be circumferentially attached to the steering collar 309, at different circumferential positions than described hereinabove, depending on the steering directions needed for a given device. Still further, it should be recognized that the endoscope shaft 20 may, in still further embodiments, have more or less than four steering wires extending longitudinally therethrough, depending on the steering capability needed for a given device.

There are a variety of different manufacturing techniques that may be employed so as to embed the camera electrical cable 301 and the steering wires 302a, 302b, 302c, 302d, within the wall structure of the endoscope shaft 20, e.g., extrusion, precision molding, etc. However, these manufacturing techniques may result in the wall structure of the endoscope shaft 20 being relatively bulky or thick. As a result, the outer diameter of the endoscope shaft 20 may be undesirably large, increasing the likelihood that a patient may experience physical discomfort due to a large-diameter endoscope being inserted into the nose, through the sinus cavities and down into the esophagus. Also as a result, in order to keep the outer diameter of the endoscope shaft smaller, the thick or bulky wall structures may force the inner diameter of the working channel to be made undesirably smaller, thereby making it more difficult for instruments to be inserted into and through the working channel. Thus, traditional manufacturing techniques for the endoscope shaft may prevent the resulting endoscopes from being suitable candidates for certain procedures, e.g., pediatric trans-nasal endoscopy procedures.

The trans-nasal endoscope 10 described hereinbelow, however, according to various embodiments, provides an improved structure and method for embedding at least one wire, e.g., the camera electrical cable 301 and/or the steering wires 302a, 302b, 302c, 302d, within the wall structure of the endoscope shaft 20. According to various embodiments, the endoscope shaft 20 is manufactured using a braiding technique which weaves filaments around the working channel 30, as well as alternately over and under the camera electrical cable 301 and the steering wires 302a, 302b, 302c, 302d. As will be described in further detail below, this over/under braiding process provides an arrangement that minimizes the outer diameter of the endoscope shaft 20, e.g., to reduce the physical and mental discomfort to patients, while simultaneously maximizing the diameter of the working channel 30, e.g., to provide the largest possible channel through which tools may be introduced, all while simultaneously providing, e.g., four-way, shaft steering capabilities as well as imaging functionality.

According to embodiments, the endoscope shaft 20 is manufactured using, e.g., 16 filaments, that are woven by, e.g., 16 bobbins, around the various components of the endoscope shaft 20 via a mandrel, the mandrel travelling longitudinally along the length of the endoscope shaft 20 during its manufacture. Of course, it should be recognized that other braiding patterns, as well as other braiding or weaving equipment, may additionally or alternatively be employed in order to manufacture the endoscope shaft 20.

In the embodiment shown, in order to manufacture the endoscope shaft 20, the various components of the endoscope shaft, e.g., the camera electrical cable 301 and the four steering wires 302a, 302b, 302c, 302d, are arranged longitudinally along the length working channel 30 in, e.g., the circumferential positions described hereinabove or, in other embodiments, in other circumferential positions. In the embodiment shown herein, a given filament of the braiding structure is wound laterally over, e.g., so as to be at a position that is laterally outside of or diametrically further from the working channel 30 than, the camera electrical cable 301. This first filament is then wound laterally over, e.g., so as to be at a position that is laterally outside of or diametrically further from the working channel 30 than, the first steering wire 302a. This first filament is then wound laterally under, e.g., so as to be at a position that is laterally inside of or diametrically closer to the working channel 30 than, the second steering wire 302b, such that the first filament is positioned between the outside surface of the working channel 30 and the second steering wire 302b. This first filament is then wound laterally over, e.g., so as to be at a position that is laterally outside of or diametrically further from the working channel 30 than, the third steering wire 302c. This first filament is then wound laterally under, e.g., so as to be at a position that is laterally inside of or diametrically closer to the working channel 30 than, the fourth steering wire 302d, such that the first filament is positioned between the outside surface of the working channel 30 and the fourth steering wire 302d. This first filament is then again wound laterally over, e.g., so as to be at a position that is laterally outside of or diametrically further from the working channel 30 than, the camera electrical cable 301. In embodiments, the first filament is then woven through this same pattern repeatedly, until the first filament has reached to farthest longitudinal end of the endoscope shaft 20.

Additionally or alternatively, in the embodiment shown herein, a second given filament is wound in a different pattern, or more specifically, around the various components of the endoscope shaft 20 in a different placement, so that the collection of all filaments employed to create the braided pattern eventually fix the camera electrical cable 301, the four steering wires 302a, 302b, 302c, 302d, and the working channel in lateral and circumferential position relative to each other. For example, in the embodiment shown, a second given filament is wound laterally over, e.g., so as to be at a position that is laterally outside of or diametrically further from the working channel 30 than, the camera electrical cable 301. This second filament is then wound laterally under, e.g., so as to be at a position that is laterally inside of or diametrically closer to the working channel 30 than, the first steering wire 302a, such that the second filament is positioned between the outside surface of the working channel 30 and the first steering wire 302a. This second filament is then wound laterally over, e.g., so as to be at a position that is laterally outside of or diametrically further from the working channel 30 than, the second steering wire 302b. This second filament is then wound laterally under, e.g., so as to be at a position that is laterally inside of or diametrically closer to the working channel 30 than, the third steering wire 302c, such that the second filament is positioned between the outside surface of the working channel 30 and the third steering wire 302c. This second filament is then wound laterally over, e.g., so as to be at a position that is laterally outside of or diametrically further from the working channel 30 than, the fourth steering wire 302d. This second filament is then again wound laterally over, e.g., so as to be at a position that is laterally outside of or diametrically further from the working channel 30 than, the camera electrical cable 301.

Advantageously, the various filaments that comprise the braided structure of the endoscope shaft 20 are each woven around the working channel 30 and the other components of the endoscope shaft 20 in a pattern. In an embodiment, the various filaments that comprise the braided structure of the endoscope shaft 20 are alternatingly woven in the two patterns described hereinabove. For example, in such an embodiment, the first, third, fifth, etc. filaments are woven in the first above-described pattern, while the alternating filaments, e.g., the second, fourth, sixth, etc. filaments, are woven in the second above-described pattern. Employing different weaving patterns for different filaments, e.g., such as by alternating them as described herein above such that some filaments are woven over and some filaments are woven under each of the electrical cable and/or the steering wires, improves the stability of the endoscope shaft 20 while simultaneously minimizing the wall thickness of the endoscope shaft 20, and thereby minimizing the outer diameter of the endoscope shaft 20. Of course, it should be recognized that other weaving patterns other than those described above may be employed, and the filaments employed to create the braided structure of the endoscope shaft 20 may be woven in a different arrangement or order than described hereinabove.

It should also be recognized that, while the braiding patterns set forth hereinabove were described as having the first filament engage the camera electrical cable 301 first, e.g., starting at a 12 o'clock or 0 degree circumferential position, this is merely exemplary. Other starting points, other than over the camera electrical cable 301, and at different circumferential positions, are also contemplated. For example, while the braiding patterns set forth above describe a first filament starting to be woven from over the camera electrical cable 301, e.g., from a 12 o'clock or 0 degree circumferential position, the other filaments in that same braiding pattern would start to be woven at different circumferential positions depending, e.g., on the number of filaments employed in that particular braiding pattern. By way of example, in a braiding pattern that employs, e.g., 16 filaments, to create its woven pattern, each filament could start its respective pattern equidistantly around the circumference of the endoscope shaft 20, e.g., a first filament starting its respective weaving pattern at a 0 degree circumferential position, a second filament starting its respective weaving pattern at a 22.5 degree circumferential position, etc. Of course, any such braiding pattern or filament spacing may be employed to minimize the wall thickness of the endoscope shaft 20 and thereby minimize the outer diameter thereof.

FIG. 4 also illustrates that, disposed around the filament 303a, 303b, etc., collectively the braided filaments 303, is a laminate layer 304. The laminate layer 304 may have various different functions. For example, the laminate layer 304 may function to protect the braided filaments 303, e.g., from breakage due to contact with sharp or other potentially physically damaging elements. The laminate layer 304 may also function to protect the internal components of the endoscope shaft 20, e.g., particularly the camera electrical cable 301 and the illumination source and imagine device, from damage due to, e.g., moisture.

Advantageously, according to various embodiments, the endoscope shaft 20 may provide different amounts of flexibility along its longitudinal length. In embodiments, the endoscope shaft 20 described herein provides such different amounts of flexibility along its longitudinal length by having, along its longitudinal length, sections for which the laminate layer 304 has different characteristics. For example, the endoscope shaft 20 described herein may provide such different amounts of flexibility along its longitudinal length by having sections for which the laminate layer 304 has different flexibilities/rigidities.

For example, in an embodiment, the endoscope shaft 20 may have a section near its distal end 44 for which the laminate layer 304 is relatively flexible relative to the other longitudinal sections of the endoscope shaft 20, thereby imparting additional flexibility to this longitudinal section of the endoscope shaft 20. This increased relative flexibility of the longitudinal section near the distal end 44 could enable the distal end 44 of the endoscope shaft 20 to be better steered, e.g., by the shaft steering mechanism 56 and the steering wires 302a, 302b, 302c, 302d, more easily by a user. Additionally or alternatively, in an embodiment, the endoscope shaft 20 may have a section nearer to its handle 50 for which the laminate layer 304 is relatively more rigid relative to the other, e.g., distal, longitudinal sections of the endoscope shaft 20, thereby imparting additional rigidity to this longitudinal section of the endoscope shaft 20. This increased relative rigidity of the section nearer to the handle 50 could enable the more proximal end of the endoscope shaft 20 to more easily maintain its shape during use.

The endoscope shaft 20 having different amounts of flexibility along its longitudinal length may be beneficial for several reasons. For example, and as set forth above, transnasal endoscopy procedures require an endoscope shaft to be inserted into the nasal passages of a patient, through the patient's sinus cavities and down into the patient's esophagus. This path is winding and curved and is lined with the patient's sensitive tissues, traditionally resulting in an undesirably high likelihood that an endoscope shaft inserted therethrough could detrimentally irritate or injure the patient. This discomfort to the patient also increases the likelihood that a patient would discontinue a procedure that has already begun, and/or the expectation of discomfort could cause a patient to avoid the procedure altogether. Knowing or anticipating the patient's discomfort, the surgeon may also experience increased anxiety and/or it may potentially negatively impact the surgeon's performance of the procedure. By increasing the relative flexibility of the endoscope shaft 20 at or near to its distal end 44 and thereby rendering the distal end 44 more steerable, a surgeon may be able to decrease the likelihood that the distal end 44 irritates or injures the patient's soft tissues when the distal end 44 of the endoscope 20 is being introduced into the patient's nasal cavity and is being maneuvered through the winding path within the patient. Additionally or alternatively, by increasing the relative rigidity of the endoscope shaft 20 at or nearer to its handle 50 and thereby rendering the proximal end of the endoscope shaft 20 more stable, a surgeon may be able to decrease the likelihood that the proximal end of the endoscope shaft 20 moves and thereby irritates or injures the patient's soft tissues when the endoscope shaft 20 is in position within the patient's nasal cavity etc. Still further, by increasing the relative rigidity of the endoscope shaft 20 at or nearer to its handle 50 and thereby rendering the proximal end of the endoscope shaft 20 more stable, a surgeon may be better able to feed the endoscope shaft 20 into the patient's nasal cavity without the proximal end of the endoscope shaft 20 collapsing or undesirably bending, thereby improving the ability for the endoscope shaft 20 to be controlled during insertion.

Figure 5:
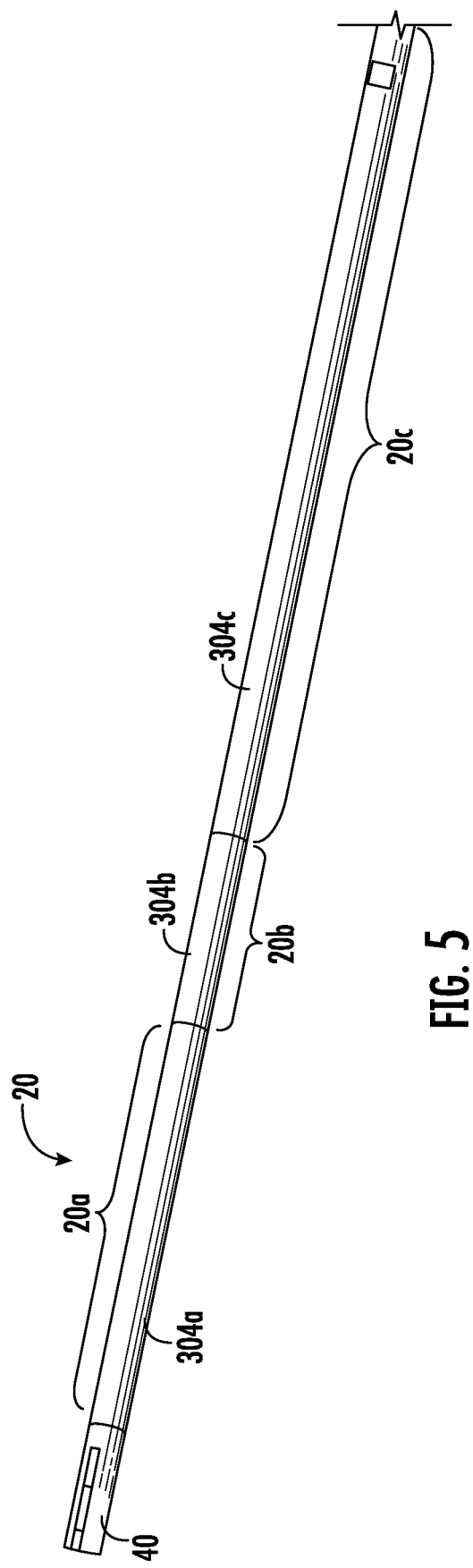
FIG. 5 illustrates an endoscope shaft having different types of laminate layer, in accordance with various embodiments.

Accordingly, in various embodiments, the endoscope shaft 20 described herein may employ two or more different types of laminate layer 304 at different longitudinal sections thereof. FIG. 5 illustrates an example embodiment in which the endoscope shaft 20 described herein may employ three different types of laminate layer 304 at different longitudinal sections thereof. Specifically, FIG. 5 illustrates a first laminate layer 304a which envelops a first, e.g., distal, endoscope shaft section 20a that is adjacent to or near a distal end 44 of the endoscope shaft 20. In addition, FIG. 5 illustrates a second laminate layer 304b which envelops a second, e.g., central, endoscope shaft section 20b that is proximal relative to the first endoscope section 20a of the endoscope shaft 20. Still further, FIG. 5 illustrates a third laminate layer 304c which envelops a third, e.g., proximal, endoscope shaft section 20a that is proximal relative to the second endoscope section 20b of the endoscope shaft 20 and adjacent to or near the handle 50 (not shown).

In this embodiment, the first laminate layer 304a may comprise a relatively flexible polymer (flexibility being measurable by any commonly employed test for same, e.g., elastic modulus or Young's modulus, as is well known by persons of skill in the art). For example, the first laminate layer 304a may comprise, e.g., Pebax® 35D (Pebax® being a tradename for a thermoplastic elastomer of polyether block amide, obtained by, e.g. polycondensation of a carboxylic acid polyamide with an alcohol termination polyether, available commercially from, e.g., Compounding Solutions in Lewiston, ME). By enveloping the first endoscope shaft section 20a with a first laminate layer 304a that is comprised of a relatively flexible polymer such as Pebax® 35D, the first endoscope shaft section 20a may enable that section of the endoscope shaft 20 to be more easily steered by a user.

In this embodiment, the second laminate layer 304b may comprise a polymer that is still flexible but is somewhat less flexible than the first laminate layer 304a. For example, the second laminate layer 304b may comprise, e.g., Pebax® 55D. By enveloping the second endoscope shaft section 20b with a second laminate layer 304b that is comprised of a lesser flexible polymer such as Pebax® 55D, the second endoscope shaft section 20b may enable that section of the endoscope shaft 20 to still be bendable as it travels through the patient's various soft tissues, but also enables it to be more stable so it can be fed into the patient's nasal cavity by a user without undesirably collapsing or sagging.

Still further, in this embodiment, the third laminate layer 304c may comprise a polymer that is again still flexible but is somewhat less flexible still than the second laminate layer 304b. For example, the third laminate layer 304c may comprise, e.g., Pebax® 72D or a suitable polyimide. By enveloping the third endoscope shaft section 20c with a third laminate layer 304c that is comprised of a still less flexible polymer such as Pebax® 72D or polyimide, the third endoscope shaft section 20c may enable that section of the endoscope shaft 20 to still be somewhat bendable if it were to travel through the patient's various soft tissues, but also enables it to be even more stable so, as it is used to feed the more distal sections of the endoscope shaft 20 into the patient's nasal cavity, the third endscope shaft section 20c is rigid enough to be pushed on by a user without it collapsing or sagging. Of course, the endoscope 10 may have more than three longitudinal sections, depending on the degrees of varying flexibility needed along the length of the endoscope shaft 20.

Figure 6:
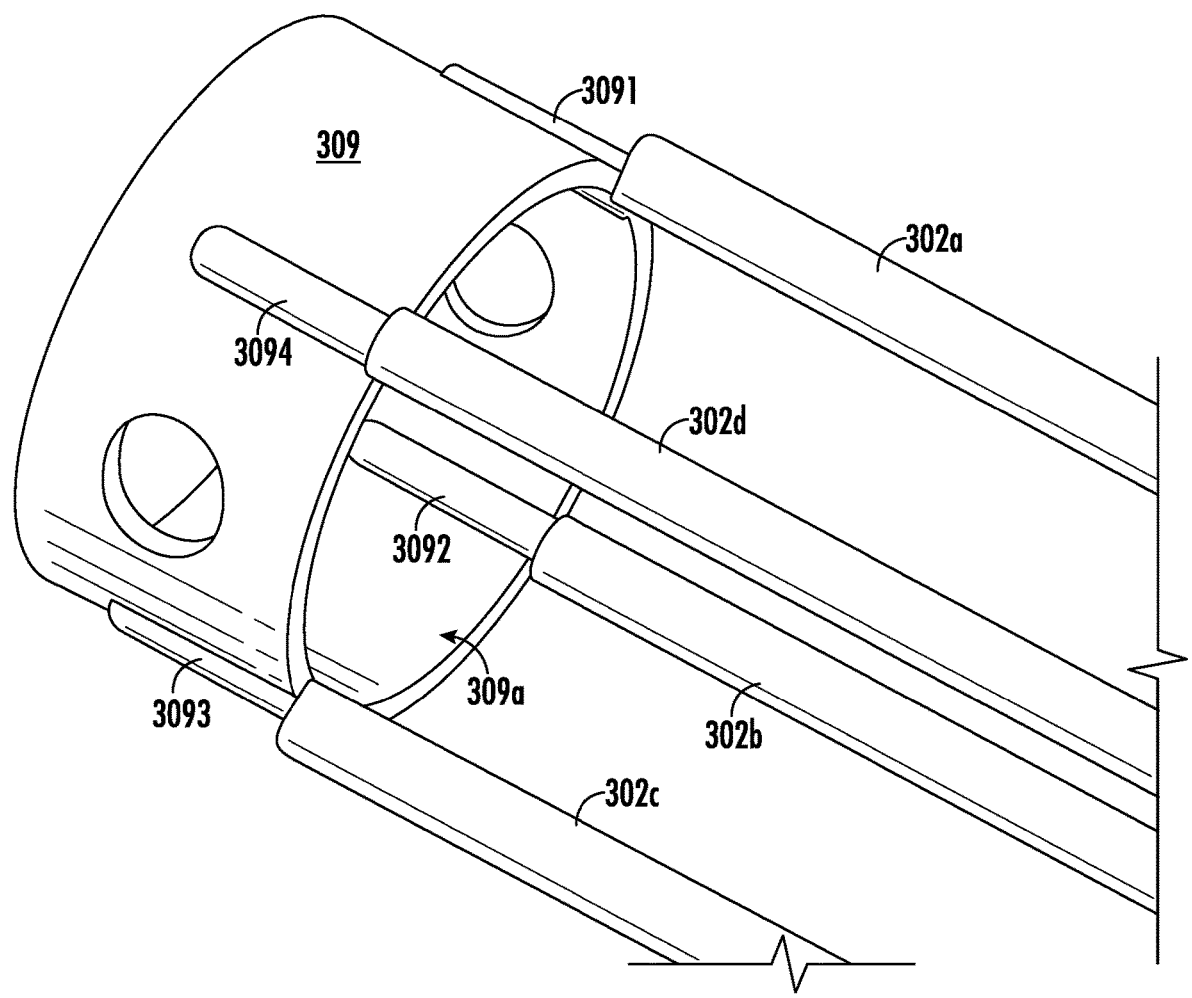
FIG. 6 illustrates a steering collar, in accordance with various embodiments.

As set forth above, the handle 50 may include a shaft steering mechanism 56 to control the lateral displacement at the distal end 40 of the endoscope shaft 20. In the embodiment shown in FIG. 4, the handle 50 includes four steering wires 302a, 302b, 302c, 302d disposed within the wall of the endoscope shaft 20 and positioned 90 degrees apart relative to each other. FIG. 6 illustrates an example embodiment of a steering collar 309. The steering collar 309 may be configured with, e.g., a ring-like structure. The steering collar 309 may be embedded within the wall of the endoscope shaft 20, e.g., it may be enclosed in the wall of the endoscope shaft 20 by having the braiding filaments woven therearound.

The steering collar 309 has an interior opening 309a through which the working channel 30 passes. In addition, the steering collar 309 may have various connection points at which the various steering wires are connected. For example, in the embodiment shown, the steering collar 309 has a first connection point 3091 for the first steering wire 302a. The first connection point 3091 is located at, e.g., a 45 degree clockwise position relative to the top-most position along the outer circumference of the working channel 30. Thus, the first connection point 3091 is advantageously located at a circumferential position relative to the working channel 30 that is the same as the circumferential position of the first steering wire 302a as it extends along the full length of the endoscope shaft 20.

In the embodiment shown, the steering collar 309 also has second, third, and fourth connection points 3092, 3093, and 3094 for connecting the steering collar 309 to the second, third and fourth steering wires 302b, 302c and 302d, respectively. The second, third, and fourth connection points 3092, 3093, and 3094 are located at, e.g., 135, 225 and 315 degree clockwise circumferential positions, respectively, relative to the top-most position along the outer circumference of the working channel 30. Thus, the second, third, and fourth connection points 3092, 3093, and 3094 are advantageously located at respective circumferential positions relative to the working channel 30 that are the same as the respective circumferential positions of the second, third and fourth steering wires 302b, 302c, 302d as they extend along the full length of the endoscope shaft 20.

The opposite ends of the steering wires 302a, 302b, 302c, 302d pass through the handle 50 and are connected to the shaft steering mechanism 56. Specifically, in the embodiment described hereinabove, the opposite, e.g., proximal, ends of the steering wires 302a, 302b, 302c, 302d pass through the distal end of the handle 50 and are connected to steering structures located within the proximal end of the handle 50. Each of the steering structures are connected to one or more of the first knob 561 and/or the opposing roller knobs 562a, 562b, which enable a user to actuate the internal steering structures and thereby move, e.g., pull, the steering wires 302a, 302b, 302c, 302d for controlling movements of the distal end 40 of the endoscope shaft 20.

Figure 7A:
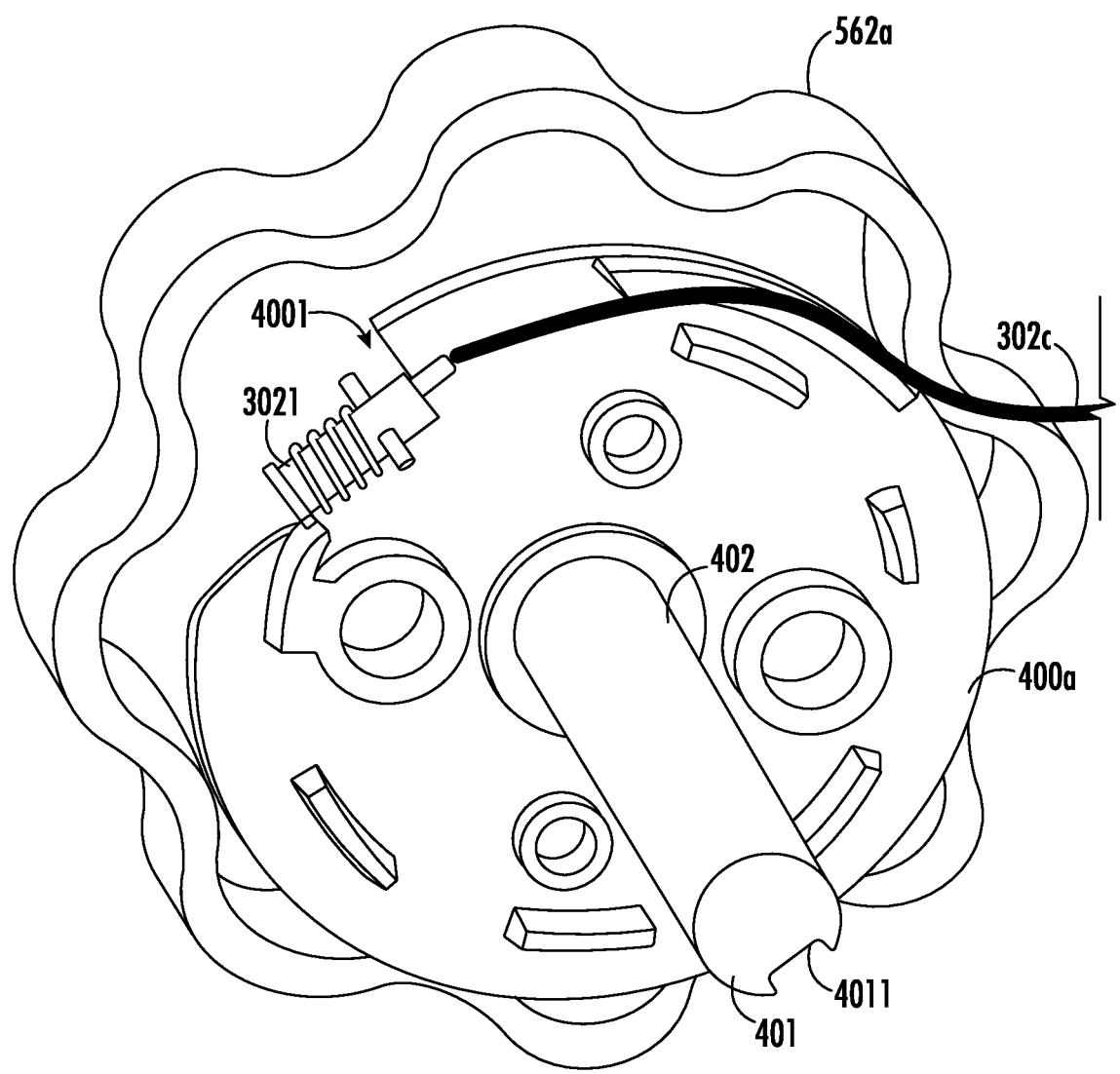
FIG. 7a is a perspective view from one side of the handle, in accordance with various embodiments.
Figure 7B:
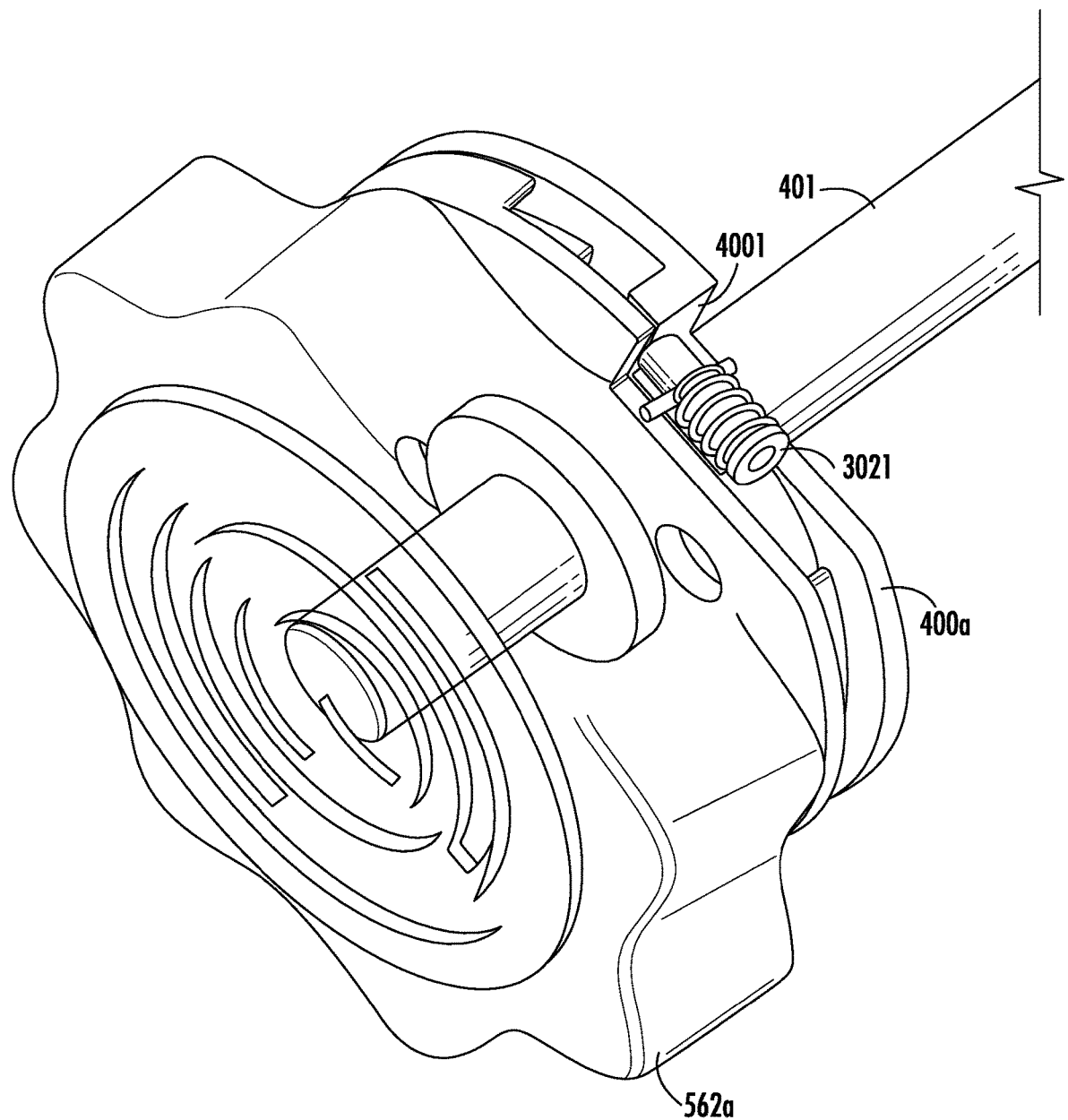
FIG. 7b is a perspective view from the opposite side of the handle, in accordance with various embodiments.

FIGS. 7a and 7b are partial perspective views (with most of the handle 50 and associated structures hidden so as not to obscure the view of various steering structures) that illustrate an example embodiment of an internal steering structure. FIG. 7a is a perspective view from one side of the handle 50, while FIG. 7b is a perspective view from the opposite side of the handle 50. Referring to FIG. 7a, there is shown a first internal steering structure in the form of a first roller wheel 400a. The first roller wheel 400a resides within the interior of the handle 50 and is generally adjacent to the inside surface of the wall of the handle 50 (the wall of the handle 50 being hidden in this view). FIG. 7a also shows a first roller knob 562a. The first roller knob 562a resides outside of the wall of the handle 50 and is generally adjacent to the outside surface of the side wall of the handle 50 (again, the wall of the handle 50 being hidden in this view).

Although not shown in these views (so as not to obscure the view of the first set of steering structures), the shaft steering mechanism 56 of the trans-nasal endoscope 10, according to various embodiments, may also include a second set of steering structures. In the trans-nasal endoscope 10 shown and described hereinabove, the second set of steering structures may be mirror images of the first roller wheel 400a and the first roller knob 562a. Specifically, the shaft steering mechanism 56 may include a second roller wheel which is located on the opposite side of the handle 50 as compared to the first roller wheel 400a, the second roller wheel also residing within the interior of the handle 50 and being generally adjacent to the inside surface of the opposite wall of the handle 50. In addition, the shaft steering mechanism 56 may also include a second roller knob 562b which is located on the opposite side of the handle relative to the first roller knob 562a, the second roller knob also residing outside of the handle 50 and being generally adjacent to the outside surface of the opposite wall of the handle 50.

It should be understood that, because the first and second steering structures, in the embodiment shown herein, are mirror images of each other, the features of the first steering structure have symmetrical features in the second steering structure. Having the first and second steering structures be symmetrical, e.g., and on opposite sides of the handle 50 relative to each other, enables ambidextrous operation of these steering structures. Furthermore, because the first and second steering structures are mirror images of each other, the operation of the first steering structure may result in simultaneous and symmetrical operation of the second steering structure, and vice versa. Thus, for the purposes of illustration, the features and operation of the first steering structures, e.g., the first roller wheel 400a and the first roller knob 562a, will be described below, recognizing that such features and operations may result in similar operation of the second steering structures, e.g., the second roller wheel and the second roller knob.

Referring again to FIGS. 7a and 7b, the roller wheel 400a defines an opening 402a at its center. A shaft 401 resides within the opening 402a of the roller wheel 400a. The shaft 401 extends laterally through both sides of the handle 50 (not shown in this view), such that a first end of the shaft 401 is connected to the first roller knob 562a as shown in FIG. 7a, while the second end of the shaft 401 is connected to the second roller knob (which is hidden in this view). In this embodiment, the shaft 401 has a key feature 4011 which mates with corresponding key features (not shown) on the first roller wheel 400a and the first roller knob 562a (likewise, though not shown in this view, the key feature 4011 of the shaft 401 may also mate with corresponding key features on the second roller wheel and the second roller knob). In this way, rotation by a user of the first roller knob 562a causes the shaft 401 to rotate, which thereby also causes the first roller wheel 400a, the second roller wheel and the second roller knob to also rotate. Likewise, because they are all keyed to the shaft 401, rotation by a user of the second roller knob also causes the second roller wheel, the first roller wheel 400a and the first roller knob 562a to also rotate.

In the embodiment shown, each of the first and second roller wheels has a respective steering wire attached thereto. For example, as shown in FIG. 7a, the first roller wheel 400a is connected to the proximal end of the third steering wire 302c. More specifically, the proximal end of the third steering wire 302c has a crimp 3021 which fixedly attaches it into a slot 4001 on the outer circumference of the first roller wheel 400a. Thus, rotation by a user of the first roller knob 562a causes rotation of the first roller wheel 400a, which in turn causes the proximal end of the third steering wire 302c to be pulled. Pulling the proximal end of the third steering wire 302c causes the length of the third steering wire 302c to move proximally within the shaft wall and thereby cause the steering collar 309 to move proximally at the circumferential position at which the third steering wire 302c is connected. In the embodiment shown, this proximal movement of the third steering wire 302c pulls the left side of the steering collar 309 such that the distal end 44 of the endoscope shaft 20 is steered towards the left.

As set forth above, the second set of steering structures, e.g., the second roller knob and the second roller wheel may be mirror images of the first roller wheel 400a and the first roller knob 562a. Thus, although hidden from view in FIG. 7a, the second roller wheel may be connected to the proximal end of its own corresponding steering wire, e.g., the first steering wire 302a. More specifically, the proximal end of the first steering wire 302a may have a similar crimp which fixedly attaches it into a slot on the outer circumference of the second roller wheel. In this way, rotation by a user of the second roller knob causes rotation of the second roller wheel, which in turn causes the proximal end of the first steering wire 302a to be pulled. Pulling the proximal end of the first steering wire 302a causes the length of the first steering wire 302a to move proximally within the shaft wall and thereby cause the steering collar 309 to move proximally at the circumferential position at which the first steering wire 302a is connected. In the embodiment shown, this proximal movement of the first steering wire 302a pulls the right side of the steering collar 309 such that the distal end 44 of the endoscope shaft 20 is steered towards the right.

Figure 8:
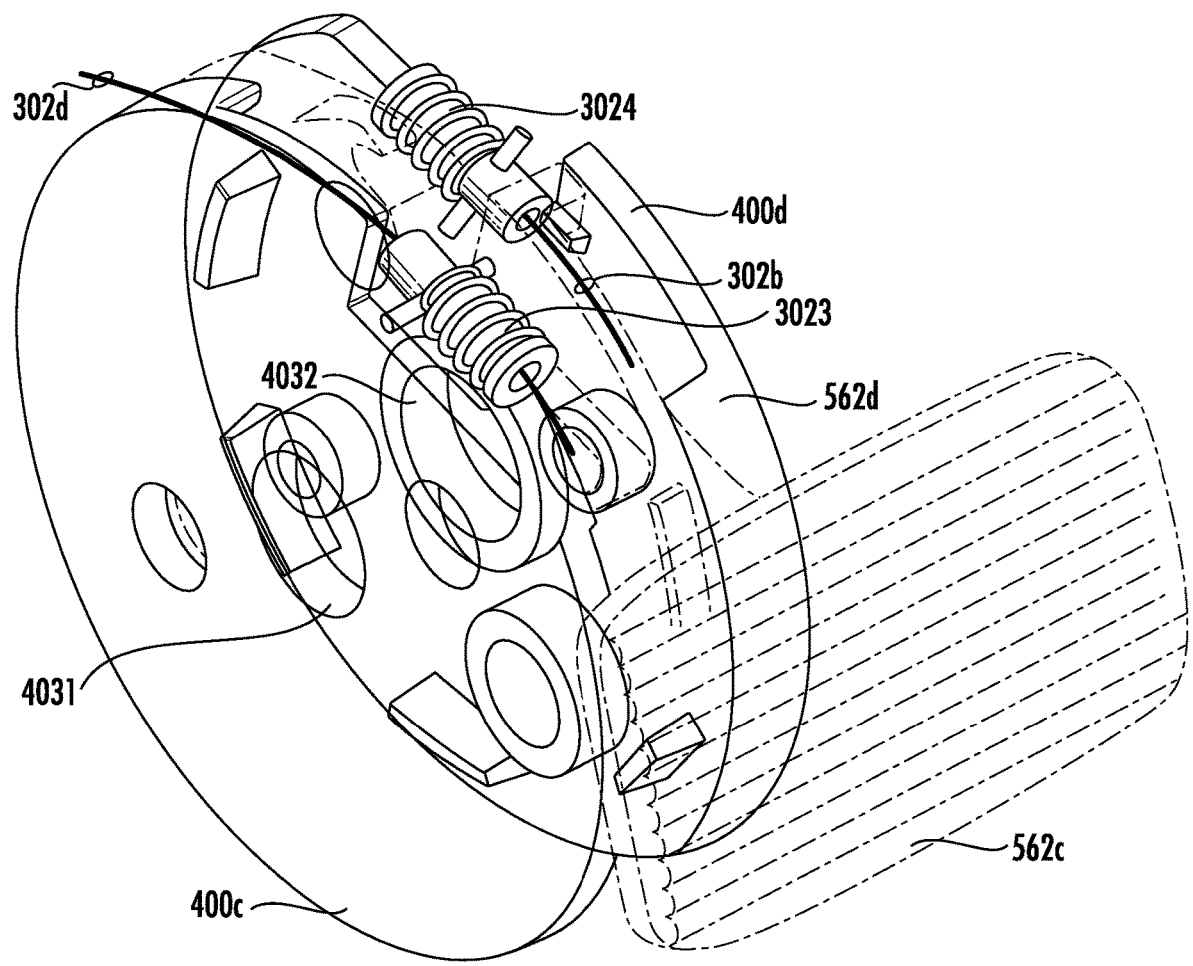
FIG. 8 illustrates steering structures that enable up and down movement of the distal end of the endoscope shaft, in accordance with various embodiments.

In addition to the shaft steering mechanism 56 including, in this embodiment, steering structures that enable left and right movement of the distal end 44 of the endoscope shaft 20, the shaft steering mechanism 56 may also include, according to various embodiments, steering structures that enable up and down movement of the distal end 44 of the endoscope shaft 20. FIG. 8 illustrates additional steering structures that enable up and down movement of the distal end 44 of the endoscope shaft 20. Specifically, FIG. 8 is a partial perspective view (with most of the handle 50 and associated structures hidden so as not to obscure the view of these steering structures) that illustrates an example embodiment of such additional internal steering structures. FIG. 8 shows a third roller wheel 400c and a fourth roller wheel 400d. The third and fourth roller wheels 400c, 400d reside within the interior of the handle 50 and between the first and second roller wheels 400a, 400b. The third roller wheel 400c is generally adjacent to the first roller wheel 400a (hidden in this view), while the fourth roller wheel 400d is generally adjacent to the second roller wheel 400b (also hidden in this view). FIG. 8 also shows a thumb knob 562c. The thumb knob 562c resides outside of the handle 50 and is generally adjacent to the outside surface of the proximal wall of the handle 50 (again, the wall of the handle 50 being hidden in this view).

Each of the third and fourth roller wheels 400c, 400d define openings 4031, 4032, respectively, at their center. The shaft 401 (shown in FIG. 7a) resides within the openings 4031, 4032 of the third and fourth roller wheels 400c, 400d. As set forth above in connection with FIG. 7a, the shaft 401 extends laterally through both side walls of the handle 50 (not shown in this view).

In this embodiment, the third and fourth roller wheels 400c, 400d are not keyed to the shaft 401 but rather the third and fourth roller wheels 400c, 400d are able to rotate freely relative to and around the shaft. The thumb knob 562c has a connector 562d that extends through the proximal wall (not shown) of the handle 50 so as to connect the thumb knob 562c to the third and fourth roller sheels 400c, 400d. In this way, rotation by a user of the thumb knob 562c causes the third and fourth roller wheel 400c, 400d to rotate about the shaft 401.

In the embodiment shown, each of the third and fourth roller wheels 400c, 400d has a respective steering wire attached thereto. For example, as shown in FIG. 8, the third roller wheel 400c is connected to the proximal end of the fourth steering wire 302d (only a portion of which is shown in FIG. 8). More specifically, the proximal end of the fourth steering wire 302d has a crimp 3023 which fixedly attaches it into a slot on the outer circumference of the third roller wheel 400c. In addition, in the embodiment shown, the fourth steering wire 302d is wound around the top (in this view) of the third roller wheel 400c. Thus, rotation by a user of the thumb knob 562c in a downward direction (in this view) causes clockwise rotation (in this view) of the third and fourth roller wheels 400c, 400d, which in turn causes the proximal end of the fourth steering wire 302d to be pulled in the proximal direction. Pulling the proximal end of the fourth steering wire 302d in the proximal direction causes the length of the fourth steering wire 302d to move proximally within the shaft wall and thereby cause the steering collar 309 to move proximally at the circumferential position at which the fourth steering wire 302d is connected. In the embodiment shown, this proximal movement of the fourth steering wire 302d pulls the top of the steering collar 309 such that the distal end 44 of the endoscope shaft 20 is steered upwardly.

As also shown in FIG. 8, the fourth roller wheel 400d is connected to the proximal end of the second steering wire 302b (only a portion of which is shown in FIG. 8). More specifically, the proximal end of the second steering wire 302b has a crimp 3024 which fixedly attaches it into a slot on the outer circumference of the fourth roller wheel 400d. In addition, in the embodiment shown, the second steering wire 302b is wound around the bottom (in this view) of the fourth roller wheel 400d. Thus, rotation by a user of the thumb knob 562c in an upward direction (in this view) causes counter-clockwise rotation (in this view) of the third and fourth roller wheels 400c, 400d, which in turn causes the proximal end of the second steering wire 302b to be pulled in the proximal direction. Pulling the proximal end of the second steering wire 302b in the proximal direction causes the length of the second steering wire 302b to move proximally within the shaft wall and thereby cause the steering collar 309 to move proximally at the circumferential position at which the second steering wire 302b is connected. In the embodiment shown, this proximal movement of the second steering wire 302b pulls the bottom of the steering collar 309 such that the distal end 44 of the endoscope shaft 20 is steered downwardly.

Of course, the above-described arrangement of the steering mechanism 56 is merely one possible such arrangement, and other mechanisms for effectuating the steering of the distal end 44 of the endoscope shaft 20 are also contemplated. For example, steering structures other than, e.g., the above-described roller wheels and roller knobs, may be employed to actuate the left and right movement of the distal end 44 of the endoscope shaft 20. Likewise, steering structures other than, e.g., the above-described roller wheels and thumb knob, may be employed to actuate the up and down movement of the distal end 44 of the endoscope shaft 20. Furthermore, there may be less than or more than the four steering wires illustrated in the embodiment described hereinabove, depending on the number of different directions of movements desired for the distal end 44 of the endoscope shaft 20. Still further, the steering wires may be connected in different circumferential locations around the steering collar 309 such that the steering mechanisms employed in the handle 50 use the steering wires to pull the steering collar 309 in different directions.

There are no limitations in terms of the particular embodiments described in this application, which are intended as illustrations of various aspects only. Many modifications and variations can be made without departing from its spirit and scope, as will be apparent to those skilled in the art. Functionally equivalent methods and apparatuses, in addition to those enumerated herein, will be apparent to those skilled in the art from the foregoing descriptions. Such modifications and variations are intended to fall within the scope of the appended claims. Only the terms of the appended claims are intended to be limiting, along with the full scope of equivalents to which such claims are entitled. It is also to be understood that the terminology used herein, e.g., "and", "or", "including", "at least" as well as the use of plural or singular forms, etc., is for the purpose of describing examples of embodiments and is not intended to be limiting.

What is claimed is:

1. An endoscope for use in a surgical procedure, comprising:
    a handle defining an outer wall that, when the handle is oriented in a first position, includes top and bottom outer walls and opposing outer left and right side walls, the handle for gripping by a user and including two rotatable roller knobs rotatable about a lateral shaft within the handle and residing outside of the outer wall of the handle and generally adjacent to an outside surface of the opposing outer left and right side walls of the handle, the handle also including a rotatable thumb knob rotatable about the same lateral shaft; and
    a steerable shaft extending from the handle, the two rotatable roller knobs configured to rotate together so as to actuate left and right steering of the steerable shaft while the handle is maintained in the first position and without changing the orientation of the handle from its first position, the rotatable thumb knob configured to control up and down steering of the steerable shaft, the shaft having a working channel extending longitudinally therethrough, the shaft having a proximal region at or adjacent to the handle and a distal region configured to be inserted into a patient, the exterior of the shaft being protected by a laminate layer,
    wherein the laminate layer of the proximal region of the shaft has a first flexibility and the laminate layer of the distal region of the shaft has a second flexibility that is more flexible than the first flexibility, such that the distal region of the shaft is more flexible than the proximal region of the shaft when the shaft is steered by the two rotatable steering knobs.

2. The endoscope of claim 1, wherein the shaft has a shaft wall having an inner diameter defined by the working channel and an outer diameter that is adjacent to and enclosed by the laminate layer, the shaft wall being comprised of braided filaments.

3. The endoscope of claim 1, wherein the shaft is configured for use in pediatric trans-nasal endoscopy procedures.

4. The endoscope of claim 1, wherein the shaft has a central region longitudinally between the proximal region and the distal region, the laminate layer of the central region having a flexibility that is more flexible than the first flexibility of the proximal regions of the shaft, and that is less flexible than the second flexibility of the distal region.

5. The endoscope of claim 4, wherein the laminate layer of the distal region is Pebax® 35D, the laminate layer of the central region is Pebax® 55D, and the laminate layer of the proximal region is Pebax® 72D.

6. The endoscope of claim 1, further comprising:
    at least one steering wire extending longitudinally within the shaft and parallel to the working channel, each one of the at least one steering wire connected to one of the two rotatable roller knobs on the handle and being actuatable by user to steer at least the distal region of the shaft.

7. The endoscope of claim 1, further comprising:
    an illumination source and an imaging device located at the distal end of the shaft, the illumination source and the imaging device being connected via an electrical cable to an electronic control module on the handle, the electrical cable extending longitudinally within the shaft and parallel to the working channel.

8. The endoscope of claim 1, further comprising:
    a control mechanism in the handle actuatable by a user to selectively control the flow of at least one of air, suction or water through the working channel.

9. The endoscope of claim 1, wherein the working channel includes an instrument port through which a surgical instrument can be introduced through the working channel.

10. The endoscope of claim 1, wherein the working channel includes a bifurcation region that splits the working channel into a first channel and a second channel, the first channel having an instrument port through which a surgical instrument can be introduced into the working channel, and the second channel configured to convey at least one of air, suction or water into the working channel via a control mechanism in the handle actuatable by a user.

11. An endoscope for use in a surgical procedure, comprising:
    a handle for gripping by a user, the handle defining an outer wall that, when the handle is oriented in a first position, includes top and bottom outer walls and opposing outer left and right side walls, the handle having a steering control mechanism;
    a shaft extending from the handle, the shaft having a working channel extending longitudinally therethrough, the shaft having a distal region configured to be inserted into a patient;
    at least two steering wires extending longitudinally through the shaft and parallel to the working channel, the at least two steering wires extending from the distal region of the shaft to the steering control mechanism of the handle,
    the steering control mechanism including first and second roller wheels located outside of the respective left and right outer side walls of the handle and the first and second roller wheels configured such that actuation by a user of either roller wheel causes both roller wheels to be simultaneously rotated around a lateral shaft within the handle so as to thereby provide ambidextrous left and right steering of at least the distal region of the shaft while the handle is maintained in the first position and without changing the orientation of the handle, the steering control mechanism also including a rotatable thumb knob that is rotatable around the same lateral shaft and that is configured to control up and down steering of at least the distal region of the shaft while the handle is maintained in the first position and without changing the orientation of the handle.

12. The endoscope of claim 11, wherein the first and second roller wheels each have one of the at least two steering wires attached thereto.

13. The endoscope of claim 11, wherein the at least two steering wires including a third steering wire to which the rotatable thumb knob is attached.

14. The endoscope of claim 13, wherein the thumb knob extends from the proximal end of the handle.

15. The endoscope of claim 11, further comprising:
a steering collar located at the distal region of the shaft, the steering wires being connected to the steering collar at circumferentially spaced apart locations such that the steering wires being pulled by the actuators selectively moves such locations of the steering collar to steer the distal region of the shaft.

16. The endoscope of claim 11, further comprising:
a control mechanism in the handle actuatable by a user to selectively control the flow of at least one of air, suction or water through the working channel.

17. The endoscope of claim 11, further comprising:
an illumination source and an imaging device located at a distal end of the shaft, the illumination source and the imaging device being connected via an electrical cable to an electronic control module on the handle, the electrical cable extending longitudinally within the shaft and parallel to the working channel.

18. The endoscope of claim 11, wherein the working channel includes an instrument port through which a surgical instrument can be introduced into the working channel.

19. The endoscope of claim 11, wherein the shaft is configured for use in pediatric trans-nasal endoscopy procedures.

* * * * *